(12) United States Patent
Tillotson

(10) Patent No.: US 10,641,753 B1
(45) Date of Patent: May 5, 2020

(54) METHODS AND SYSTEMS FOR MEASURING CONCENTRATIONS OF KNOWN COMPONENTS IN GAS SAMPLES USING ACOUSTIC RESONANCE

(71) Applicant: The Boeing Company, Chicago, IL (US)

(72) Inventor: Brian Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 42 days.

(21) Appl. No.: 16/170,926

(22) Filed: Oct. 25, 2018

(51) Int. Cl.
| | |
|---|---|
| *G01N 33/00* | (2006.01) |
| *G01N 29/036* | (2006.01) |
| *G01N 29/44* | (2006.01) |
| *G01N 29/30* | (2006.01) |
| *G01N 29/34* | (2006.01) |
| *G01N 29/22* | (2006.01) |

(52) U.S. Cl.
CPC ....... *G01N 33/0062* (2013.01); *G01N 29/036* (2013.01); *G01N 29/22* (2013.01); *G01N 29/30* (2013.01); *G01N 29/34* (2013.01); *G01N 29/4436* (2013.01); *G01N 33/004* (2013.01); *G01N 33/0009* (2013.01); *G01N 33/0027* (2013.01)

(58) Field of Classification Search
CPC ...... G01N 29/036; G01N 29/12; G01N 29/22; G01N 29/221; G01N 29/34; G01N 29/4436; G01N 33/0009; G01N 33/0027; G01N 33/0062
USPC .......................... 73/23.2, 24.01, 24.06, 31.05
See application file for complete search history.

(56) References Cited

U.S. PATENT DOCUMENTS

| | | | | |
|---|---|---|---|---|
| 2002/0151789 A1* | 10/2002 | Mansy | ..................... | A61B 8/08 600/431 |
| 2007/0231872 A1* | 10/2007 | Butters | ................ | G01N 37/005 435/173.1 |

FOREIGN PATENT DOCUMENTS

| | | | | |
|---|---|---|---|---|
| CN | 104777328 | * | 7/2015 | ................ G01P 5/24 |

OTHER PUBLICATIONS

Barlea, N.M. , "Acoustic Measurement of Gas Composition", International Conference on Processes in Isotopes and Molecules, Retrieved from the Internet: https://www.researchgate.net/publication/235623593_Acoustic_measurement_of_gas_composition, 2005, 6 pgs.

(Continued)

*Primary Examiner* — Benjamin R Schmitt
(74) *Attorney, Agent, or Firm* — Kwan & Olynick LLP

(57) ABSTRACT

Disclosed are methods and systems for measuring concentration of known components in gas samples using an acoustic resonance technique. A system includes a resonant chamber, a sound generator positioned at and acoustically coupled to an opening of the resonant chamber, and an audio sensor positioned proximate to and in sound communication to the opening and configured to measure an acoustic spectrum. During operation, the sound generator produces a white noise such that the soundwaves of the white noise passes through a gas sample positioned in the resonant chamber. As the soundwaves pass through the gas sample, the audio sensor monitors the frequency spectrum and identifies any resonant frequency that, if present, would correspond to a specific component and the concentration of this component. Specifically, the component concentration is determined from the frequency response.

22 Claims, 7 Drawing Sheets

(56) References Cited

OTHER PUBLICATIONS

Pang, Sheng Yee, "Ultrasound sensor for gas concentration measurement", Master's Degree Project in Electrical Measurement Technology XR-EE-MST 2011:003 Stockholm, Sweden, Retrieved from the Internet: https://www.diva-portal.org/smash/get/diva2:511270/FULLTEXT01.pdf, 2011, 67 pgs.

* cited by examiner

METHODS AND SYSTEMS FOR MEASURING CONCENTRATIONS OF KNOWN COMPONENTS IN GAS SAMPLES USING ACOUSTIC RESONANCE

BACKGROUND

Measuring concentrations of various components (e.g., chemical elements or compounds) in gas samples often requires complex and expensive equipment. For example, oxygen concentration is typically measured using a polarographic electrode, fuel cell, and paramagnetic analyzer. Carbon dioxide concentration is measured using an infrared analyzer, molecular correlation spectrography, and photoacoustic spectrography. Other conventional techniques include mass spectrometry, Raman spectroscopy, refractometry, gas chromatography, non-dispersive infrared analysis, differential absorption light detection and ranging analysis, chemiluminescence analysis, tunable diode laser absorption spectroscopy, and the like. These techniques and corresponding devices, while precise and accurate, are costly, bulky, and often fragile. As a result of these complexities and costs, gas concentration analysis is not as widely adopted as desired, especially in the field (away from laboratories), tight spaces, and the like.

At the same time, gas concentration analysis is important from safety, process control, and other standpoints. For example, when a fuel tank is flushed with carbon dioxide ($CO_2$), it is important to determine or at least roughly estimate the concentration of carbon dioxide in the tank before a person can safely enter the tank without a breathing apparatus. In another example, the concentration of ethyl alcohol (or another solvent) in a smoothing container used for three-dimensional (3-D) printing needs to be maintained within a range. As 3-D printing gains popularity and becomes more affordable, this solvent concentration control becomes problematic. In both examples presented above, the expected components are known, and only concentrations of these components are needed.

What is needed are methods and systems for measuring concentration of known components in gas samples.

SUMMARY

Disclosed are methods and systems for measuring concentration of known components (e.g., chemical elements or compounds) in gas samples using an acoustic resonance technique. A system includes a resonant chamber, a sound generator positioned at and acoustically coupled to the opening of the resonant chamber, and an audio sensor positioned proximate to and in sound communication to the opening and configured to measure an acoustic spectrum. During operation, the sound generator produces a white noise such that the soundwaves of the white noise pass through a gas sample positioned in the resonant chamber. As the soundwaves pass through the gas sample, the audio sensor monitors the frequency spectrum and identifies any resonant frequency that, if present, would correspond to a specific component and the concentration of this component. Specifically, the component concentration is determined from the frequency response.

Illustrative, non-exclusive examples of inventive features according to present disclosure are described in following enumerated paragraphs:

A1. System 100 for measuring a concentration of a known component in a gas sample using an acoustic resonance technique, system 100 comprising:
  resonant chamber 110, comprising a wall 112, forming interior 114, and opening 116 extending through wall 112 to interior 114;
  sound generator 120, positioned at and acoustically coupled to opening 116 of resonant chamber 110 and configured to generate white noise and supply white noise into interior 114 of resonant chamber 110; and
  audio sensor 140, positioned proximate to and in sound communication to opening 116 and configured to measure an acoustic spectrum emitted from interior 114 of resonant chamber 110 through opening 116.

A2. System 100 according to paragraph A1,
  wherein wall 112 of resonant chamber 110 comprises movable portion 113, opposite of opening 116 and slidably coupled to fixed portion 115 of wall 112,
  wherein opening 116 and movable portion 113 define the length of interior 114 of resonant chamber 110; and
  wherein the length of interior 114 is controllably adjustable.

A3. System 100 according to paragraphs A1 and A2,
  wherein resonant chamber 110 comprises two or more markings; and
  wherein each of two or more markings represents a resonant wavelength, corresponding to the length of interior 114.

A4. System 100 according to paragraphs A1-A3,
  wherein wall 112 is formed by a transparent syringe; and
  wherein movable portion 113 is formed by a piston.

A5. System 100 according to paragraphs A1-A4, wherein sound generator 120 is selected from group consisting of:
  an electronic sound generator,
  a combination of a sound source 124 and an airflow generator 122; and
  a combination of a sound source 124 and an airflow supply line 125.

A6. System 100 according to paragraph A5, wherein sound source 124 is a reed.

A7. System 100 according to paragraph A5, wherein airflow generator 122 is selected from a group consisting of a syringe, a compressed air tank, and a compressor.

A8. System 100 according to paragraphs A1-A7, further comprising computer system 190 such that audio sensor 140 is a part of computer system 190 and such that resonant chamber 110 and sound generator 120 are connected to and supported by computer system 190.

A9. System 100 according to paragraph A8, wherein computer system 190 comprises controller 150 for analyzing the acoustic spectrum and determining the concentration of the known component in the gas sample.

A10. System 100 according to paragraph A8, wherein computer system 190 is a mobile phone further comprising enclosure 192; and wherein resonant chamber 110 and sound generator 120 are integrated into enclosure 192.

B1. Method 400 for measuring a concentration of a known component in a gas sample using system 100, comprising resonant chamber 110, sound generator 120, and audio sensor 140, method 400 comprising:
  receiving gas sample into interior 114 of resonant chamber 110;
  generating white noise using sound generator 120, positioned at and acoustically coupled to opening 116 of resonant chamber 110 such that white noise propagates to interior 114 of resonant chamber 110; and
  capturing an acoustic spectrum using audio sensor 140, positioned proximate to and in sound communication to opening 116, wherein the acoustic spectrum represents interaction of the white noise with the gas sample received in interior 114 of resonant chamber 110 and corresponds to the concentration of the known component in the gas sample.

B2. Method 400 according to paragraph B1, further comprising determining, from the acoustic spectrum, the concentration of the known component in the gas sample.

B3. Method 400 according to paragraph B2,
wherein determining concentration of known component in gas sample is performed using a formula $$Con_{Cont} = \frac{\left(\frac{RF_{Ref}}{RF_{Test}}\right)^2 - 1}{\frac{MM_{Cont}}{MM_{Ref}} - 1},$$

wherein $Con_{Cont}$ represents the concentration of the known component,
wherein $RF_{Ref}$ represents a resonant frequency of a reference sample tested using system 100,
wherein $RF_{Test}$ represents a resonant frequency of the gas sample in the acoustic spectrum,
wherein $MM_{Cont}$ represents a molar mass of the known component; and
wherein $MM_{Ref}$ represents a molar mass of the reference sample.

B4. Method 400 according to paragraph B1, further comprising:
determining a molar mass of the gas sample using a formula $$MM_{Test} = MM_{Ref} \times \left(\frac{RF_{Ref}}{RF_{Test}}\right)^2,$$

wherein $RF_{Ref}$ represents a resonant frequency of a reference sample tested using system 100,
wherein $RF_{Test}$ represents a resonant frequency of the gas sample in the acoustic spectrum; and
wherein $MM_{Ref}$ represents a molar mass of the reference sample; and
determining the concentration of the known component in the gas sample from the molar mass of the gas sample.

B5. Method 400 according to paragraphs B1-B4, further comprising performing a calibration of system 100 using a reference sample, thereby determining a resonant frequency of the reference sample.

B6. Method 400 according to paragraph B5, wherein the known component replaces one or more components in the reference sample, thereby forming the gas sample.

B7. Method 400 according to paragraph B5, wherein the known component proportionally replaces all components in the reference sample, thereby forming the gas sample.

B8. Method 400 according to paragraphs B1-B7, further comprising displaying the concentration of the known component in the gas sample on a user interface (UI) component 170 of system 100.

B9. Method 400 according to paragraphs B1-B8, further comprising adjusting the length of interior 114 of resonant chamber 110.

B10. Method 400 according to paragraph B9, wherein adjusting the length of interior 114 comprises changing position of movable portion 113 of wall 112 of resonant chamber 110 relative to opening 116.

B11. Method 400 according to paragraph B1-B10, wherein receiving the gas sample into interior 114 of resonant chamber 110 comprises changing the position of movable portion 113 of wall 112 relative to opening 116.

B12. Method 400 according to paragraphs B1-B11, wherein generating the white noise comprises supplying an airflow to sound source 124 of sound generator 120.

DETAILED DESCRIPTION

Figure 1:
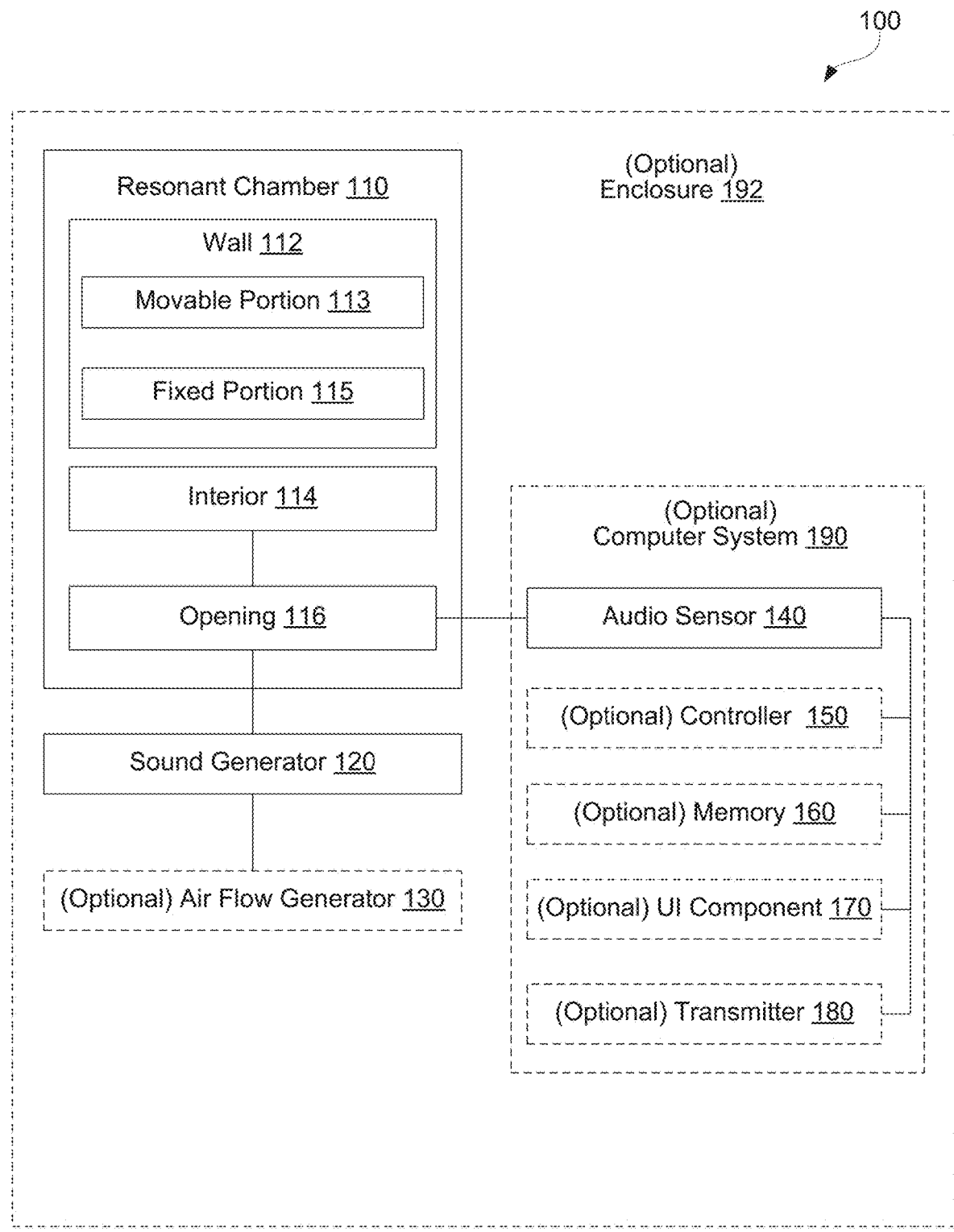
FIG. 1 is a block diagram of a system for measuring a concentration of a known component in a gas sample using an acoustic resonance technique, in accordance with some examples.

In the following description, numerous specific details are set forth in order to provide a thorough understanding of the presented concepts. In some examples, the presented concepts are practiced without some or all of these specific details. In other instances, well known process operations have not been described in detail so as to not unnecessarily obscure the described concepts. While some concepts will be described in conjunction with the specific examples, it will be understood that these examples are not intended to be limiting.

Introduction

Disclosed herein are methods and systems which utilize acoustic resonance for measuring concentration of known components (e.g., chemical elements or compounds) in gas samples. The acoustic resonance depends on the molar mass of a gas sample. A reference gas sample has one acoustic resonant frequency. When a component is added to the reference gas sample, e.g., either diluting the reference gas sample or replacing one or more components in the reference gas sample, the molar mass of the resulting gas sample changes in some examples, which also changes the acoustic resonant frequency. The change in the acoustic resonant frequency can be observed using an audio sensor. Furthermore, molar masses of the reference gas sample and of the component, which are known, allow determination of the concentration of the known component. It should be noted that the molar mass of the component is needed to determine the concentration. As such, the component should be known. Many applications of measuring gas concentrations deal with known components, such as carbon dioxide in the examples described above. Furthermore, approximate measurements of gas concentrations are often sufficient for many applications. For example, the concentration of carbon dioxide in air can be measured with a precision of +/−5% molar.

A brief description of one example of a method and a corresponding system will now be provided for context. The system includes a resonant chamber, a sound generator, and an audio sensor. In some examples, the system is first used for testing a reference gas sample of the known composition and molar mass to determine the reference resonant frequency. Prior to a test, a gas sample is supplied into the resonant chamber. The sound generator then generates white noise at the opening of the resonant chamber. For purposes of this disclosure, the white noise is defined as acoustic noise having a continuous spectrum (i.e., a spectrum with no frequency gaps) that has substantially constant power spectral density over the range of frequencies. This continuous spectrum includes resonant frequencies of the resonant chamber for a variety of gas compositions. Sound waves of the white noise pass through the gas sample in the resonant chamber, which interacts with the gas sample and causes a spike in the spectral power resonant frequency corresponding to the composition of the gas sample. Specifically, the acoustic resonant frequency (RF) is inversely proportional to the square root of molar mass (MM), as shown in Formula 1:

$$RF \sim \frac{k}{\sqrt{MM}} \quad \text{(Formula 1)}$$

This relationship between the acoustic resonant frequency and molar mass is used to determine the molar mass of the test sample and then calculate the concentration of the component (e.g., chemical elements or compounds) in that sample. Specifically, a resonant frequency of a sample with a known mass (i.e., the reference sample) is compared to a resonant frequency of a sample with an unknown molar mass (i.e., the test sample or the gas sample). Formula 2 is derived from Formula 1 and allows calculation of the molar mass of the test sample ($MM_{Test}$) using the molar mass of the reference sample ($MM_{Ref}$) multiplied by the square of the ratio of the resonant frequency of the reference sample ($RF_{Ref}$), divided by the resonant frequency of the test sample ($RF_{test}$):

$$MM_{Test} = MM_{Ref} \times \left(\frac{RF_{Ref}}{RF_{Test}}\right)^2 \quad \text{(Formula 2)}$$

Knowing the molar mass of the test sample ($MM_{Test}$), the concentration of the known component ($Con_{Cont}$) is then determined. Specifically, the known component has a known molar mass of this component ($MM_{Cont}$). Coupled with the known molar mass of the reference sample ($MM_{Ref}$), which is diluted by the component dilutes, the concentration of the known component ($Con_{Cont}$) can be found. The premise is that the total molar mass of the test sample ($MM_{test}$) is a combination of the molar masses of its components.

Formulas 3-5 apply to examples in which the reference sample has a single component and/or when multiple components of the reference sample are equally diluted/replaced by the component. In these examples, the total molar mass of the test sample ($MM_{Test}$) is presented by Formula 3:

$$MM_{Test} = (1 - Con_{Cont}) \times MM_{Ref} + Con_{Cont} \times MM_{Cont} \quad \text{(Formula 3)}$$

Formula 3 can be rearranged to solve for the concentration of the known component ($Con_{Cont}$) as shown in Formula 4:

$$Con_{Cont} = \frac{MM_{Test} - MM_{Ref}}{MM_{Conf} - MM_{Ref}} \quad \text{(Formula 4)}$$

Substituting the molar mass ($MM_{Test}$) of the test sample in Formula 4 with the one shown in Formula 2 and simplifying the equation yields Formula 5:

$$Con_{Cont} = \frac{\left(\frac{RF_{Ref}}{RF_{Test}}\right)^2 - 1}{\frac{MM_{Cont}}{MM_{Ref}} - 1} \quad \text{(Formula 5)}$$

A stated above, Formula 5 applies to examples in which the reference sample has a single component and/or when multiple components of the reference sample are equally diluted/replaced by the component. In other examples, different components of the multi-component reference sample may be affected differently by a component. In one example, a specific component of the multi-component reference sample is replaced by the component to form a test sample. For example, only oxygen, but not nitrogen, in air is replaced with carbon dioxide. These examples are described below the experimental results section of this disclosure.

Overall, to find the concentration of the known component ($Con_{Cont}$) in a test sample, one needs to know or determine the resonant frequency of a reference sample ($RF_{Ref}$), the molar mass of the reference sample ($MM_{Ref}$), and the molar mass of the known component ($MM_{Cont}$). In some examples, the resonant frequency ($RF_{Ref}$) of the reference sample is determined during a calibration operation and is supplied as a known value for this system. The resonant frequency of the test sample ($RF_{Test}$) is determined during an actual test. In some examples, the value of the resonant frequency of the test sample ($RF_{Test}$) is used directly as "Go/No Go" condition (e.g., a concentration of carbon dioxide is excessive for operation when the resonant frequency of the test sample ($RF_{test}$) is less than 109 Hz). Alternatively, the actual value of the concentration of the known component ($Con_{Cont}$) is calculated.

It should be noted that the same system (e.g., a single set of equipment) and the same method are operable to measure concentrations of a wide range of possible components in reference samples. This approach reduces equipment and operating costs in comparison to traditional methods.

System Examples

FIG. 1 is a block diagram of system 100 for measuring a concentration of a known component in a gas sample using an acoustic resonance technique, in accordance with some examples. System 100 comprises resonant chamber 110, sound generator 120, and audio sensor 140. Other optional components of system 100, such as airflow generator 130 and/or enclosure 192, are used in some examples to provide additional functionality. In some examples, computer system 190 is a part of system 100. As described below, in these examples, various components of system 100, such as sound generator 120 and audio sensor 140 are components of computer system 190 (e.g., a speaker and a microphone of a mobile phone). Resonant chamber 110, sound generator 120, and audio sensor 140 are mechanically interconnected to provide certain spatial orientation between various features of these components as further described below. For example, resonant chamber 110, sound generator 120, and audio sensor 140 are supported by enclosure 192.

Figure 2A:
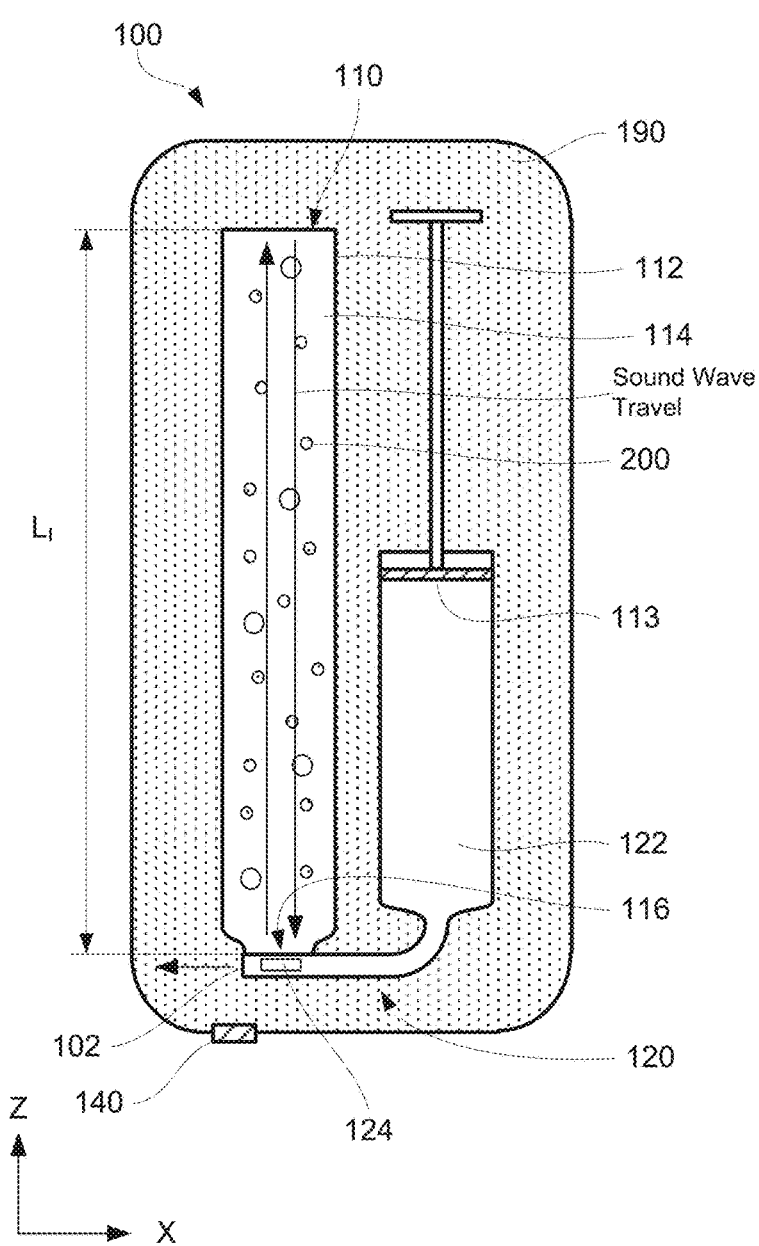
FIGS. 2A and 2B are schematic front and side views of one example of the system in FIG. 1.
Figure 3A:
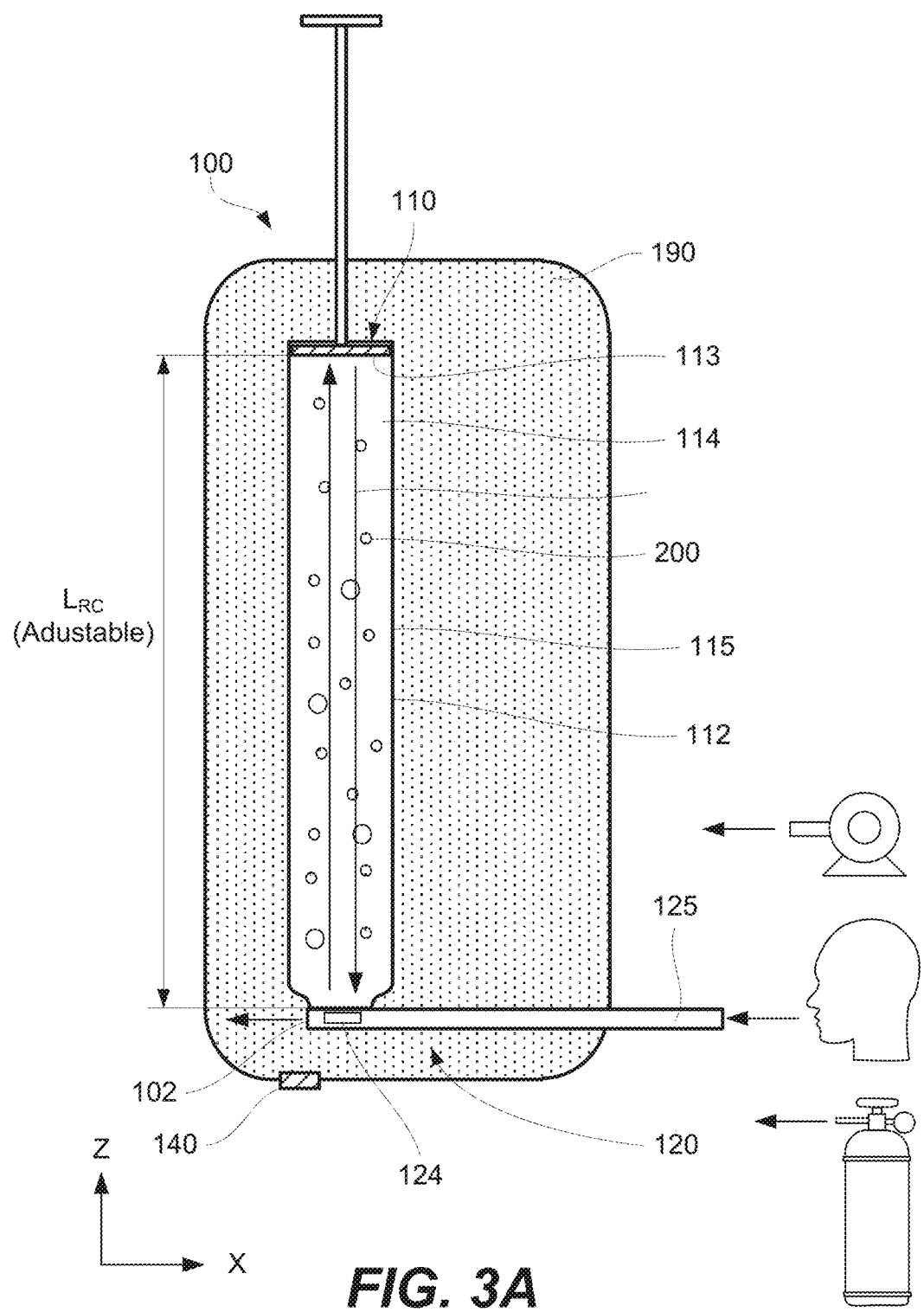
FIG. 3A is schematic front view of another example of the system in FIG. 1.
Figure 3B:
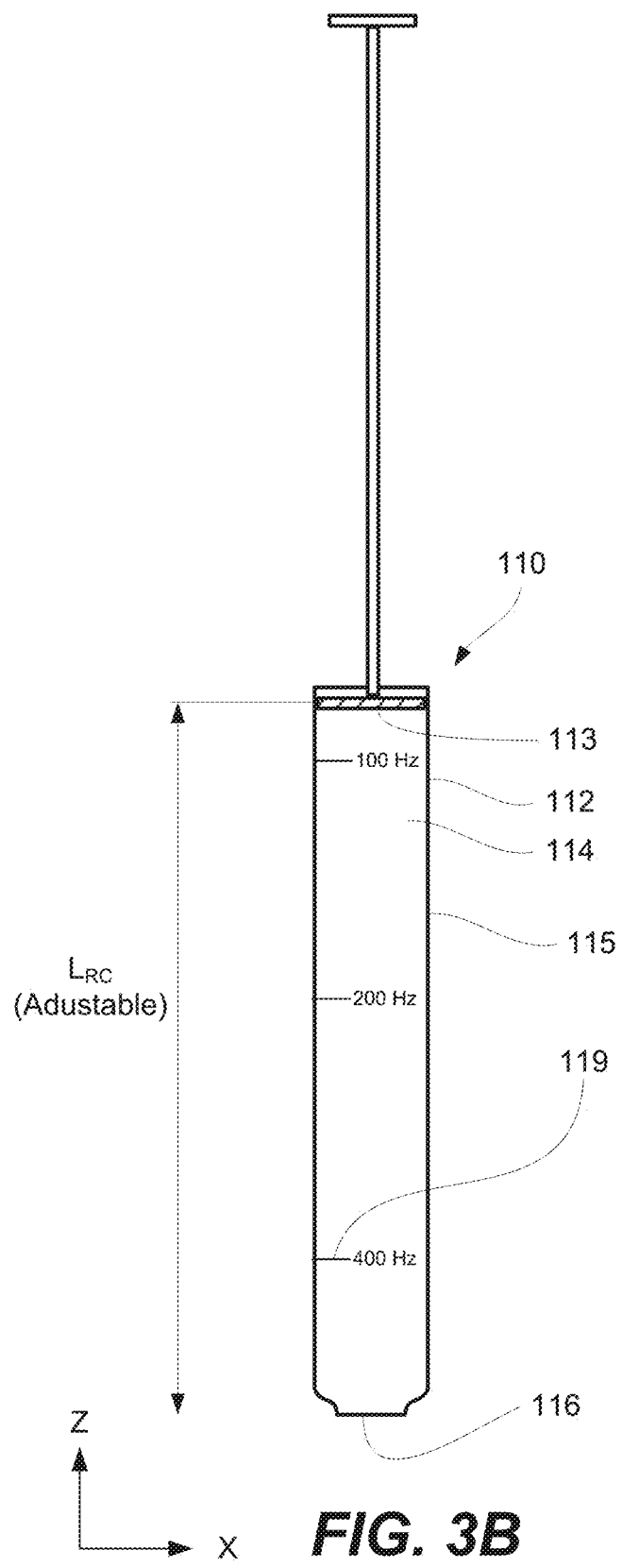
FIG. 3B is a schematic illustration of a resonant chamber of the system in FIG. 3A, in accordance with some examples.

Referring to FIGS. 2A and 3B, resonant chamber 110 comprises wall 112, forming interior 114 of resonant chamber 110. Resonant chamber 110 also comprises opening 116 extending through wall 112 to interior 114. During operation of system 100, the gas sample is positioned within interior 114. In some examples, opening 116 is used to deliver the gas sample to and/or remove the gas sample from interior 114.

Opening 116 is used for acoustic communication between the gas sample and sound generator 120 and audio sensor 140. As such, sound generator 120 and audio sensor 140 have specific positions relative to opening 116 as further described below. In some examples, opening 116 is the only opening in resonant chamber 110. The area of opening 116 is less than about 50% of the cross-sectional dimension of resonant chamber 110, measured in the plane perpendicular to the length (L 1) of resonant chamber 110. In some examples, the size of opening 116 is variable, e.g., to easily draw in a gas sample or push it out when the size is large, and reduce the size for the accurate acoustic measurement.

Wall 112 of resonant chamber 110 is rigid or semi-rigid such that soundwaves are able to bounce back from wall 112 during the analysis of gas sample 200. Some examples of materials suitable for wall 112 include, but are not limited to, metal, hard plastics, wood, or ceramic.

Referring to FIG. 2A, the distance between opening 116 and a portion of wall 112, opposite of opening 116, is an interior length ($L_I$). The interior length determines, at least in part, resonant frequencies of gas samples. In some examples, the interior length is constant. In other words, this portion of wall 112 is fixedly attached to other options of wall 112 forming opening 116. The constant length improves precision by removing human error in establishing the length. On the other hand, the variable length allows drawing the gas sample into resonant chamber 110. Furthermore, the variable length allows choosing the length where the resonant frequency is separated from the background noise, such as noise from an engine or other machine that might distort the acoustic measurement.

Alternatively, in other examples, the interior length ($L_I$) is controllably adjustable, as further described below. Referring to FIGS. 3A and 3B, in some examples, wall 112 of resonant chamber 110 comprises movable portion 113, such as a plunger. This movable portion 113 is positioned opposite of opening 116 and seals interior 114 together with fixed portion 115 (e.g., to prevent the gas sample from escaping interior 114 away from opening 116). Also, the seal allows creating a positive pressure or a negative pressure inside interior 114 when movable portion 113 is advanced relative to fixed portion 115 and changed the volume of interior 114. This feature is used to supply the gas sample into interior 114 or remove the gas sample from interior 114.

Movable portion 113 is slidably coupled to fixed portion 115 of wall 112, which defines opening 116. As such, in these examples, the position of movable portion 113 determines the interior length ($L_I$). Referring to FIG. 3B, in some examples, resonant chamber 110 comprises two or more markings 119. Each of the two or more markings 119 represents a resonant wavelength. As such, the position of movable portion 113 is adjusted to change the sensitivity of the system to different types of components. The precision of the measurement is higher if movable portion 113 is positioned away from opening 116 (increasing the length). The larger length translates into a larger volume of gas sample to fill resonant chamber 110. If only a small amount of gas sample is available, movable portion 113 is positioned close to opening 116. Furthermore, when movable portion 113 is used to draw in the gas sample, returning movable portion 113 to exactly the same position each time is difficult. The markings are used to determine the frequency corresponding to the current position of movable portion 113.

It should be noted that the resonant frequency decreases with the reciprocal of the interior length, while the volume increases linearly with the interior length. Therefore, conventional volume graduations on measuring apparatus are not representative.

In specific examples, wall 112 is formed by a transparent syringe. Movable portion 113 is formed by a piston. The transparency of wall 112 allows determining the position of movable portion 113, e.g., relative to markings 119. Other examples a cylindrical barrel with a seal or other like container.

Referring to FIG. 2A, sound generator 120 is positioned at and acoustically coupled opening 116 of resonant chamber 110. Sound generator 120 is configured to generate white noise, which has a continuous spectrum (i.e., a spectrum with no gaps) that has substantially constant power spectral density over the range of frequencies. The acoustic coupling to opening 116 allows directing the white noise from sound generator 120 to interior 114 of resonant chamber 110. In other words, during operation of system 100, sound generator 120 is also acoustically coupled to gas sample 200 provided within interior 114. The white noise interacts with gas sample 200, thereby creating a unique spectral signature of gas sample 200 as further described below.

Some examples of sound generator 120 include, but are not limited to, an electronic sound generator, a combination of sound source 124 and an airflow generator 122, and a combination of sound source 124 and an airflow supply line 125. Other examples are also within the scope. One example of the electronic sound generator is a speaker (e.g., a cellphone speaker coupled to a controller (processor)). In some examples, the electronic sound generator is set to a specific spectral range corresponding to gas sample 200.

In some examples, sound source 124 is a reed or other like device. Sound source 124 is configured to generate white noise when subjected to airflow. In some examples, the airflow is generated by a user, e.g., blowing through airflow supply line 125 as, for example, shown in FIG. 3A. FIG. 3A also shows examples of a compressed air tank, such as an air compressor (or an air blower/pump), which can also be used for generating an airflow directed at sound source 124. FIG. 2A illustrates yet another example in which airflow generator 122 is a syringe, operable by a user to generate an airflow. This syringe used as an airflow generator 122 should be distinguished from the syringe shown in FIGS. 3A and 3B, which is operable as resonant chamber 110. In some examples, system 100 comprises two syringes, with one operable as airflow generator 122 and another one operable as resonant chamber 110.

Referring to FIG. 2A, audio sensor 140 is positioned proximate to and in sound communication to opening 116. Audio sensor 140 is configured to measure an acoustic spectrum. One example of audio sensor 140 is a microphone.

In some examples, audio sensor 140 is coupled to optional controller 150, which is operable to analyze the acoustic spectrum measured by audio sensor 140. The output this of this analysis includes at least one of: a resonant frequency in the acoustic spectrum measured by audio sensor 140, a molar mass of gas sample 200, and a concentration of the known component in gas sample 200. Various operations associated with controller 150 are described below.

In some examples, audio sensor 140 and/or controller 150 are coupled to optional UI component 170. UI component 170 is configured to display at least one of: an acoustic spectrum measured by audio sensor 140, a resonant frequency in this acoustic spectrum, a molar mass of gas sample 200, a concentration of the known component in gas sample 200, and a condition corresponding to one of the above (e.g., a "go/no-go" indication). Some examples of UI component 170 include, but are not limited to, a display, a speaker, a light, a dial, and the like.

In some examples, audio sensor 140 and/or controller 150 are coupled to optional memory 160. Memory 160 is configured to store at least one of: an acoustic spectrum measured by audio sensor 140, a resonant frequency in this acoustic spectrum, a molar mass of gas sample 200, a concentration of the known component in gas sample 200, a condition corresponding to one of the above (e.g., a "go/no-go" indication), and instructions for operating controller 150.

In some examples, audio sensor 140 and/or controller 150 are coupled to optional transmitter 180. Transmitter 180 is configured to transmit and/or receive one or more of the following to another system or device: an acoustic spectrum measured by audio sensor 140, a resonant frequency in this acoustic spectrum, a molar mass of gas sample 200, a concentration of the known component in gas sample 200, a condition corresponding to one of the above (e.g., a "go/no-go" indication), and instructions for operating controller 150.

Figure 2B:
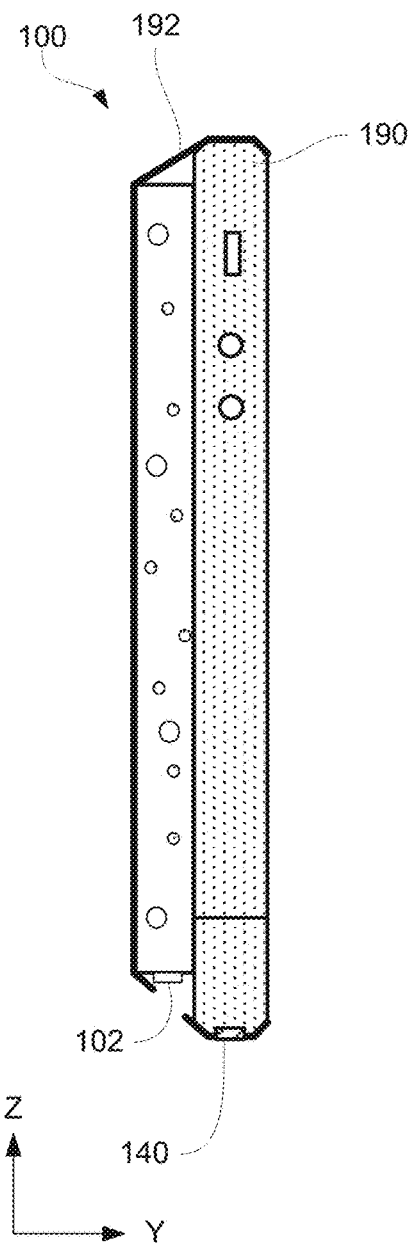

Referring to FIG. 1, in some examples, system 100 further comprises computer system 190. In more specific examples, audio sensor 140 is part of computer system 190. Resonant chamber 110 and sound generator 120 are connected to computer system 190. FIGS. 2A and 2B illustrate an example in which computer system 190 is a mobile phone, which has enclosure 192. Resonant chamber 110 and sound generator 120 are integrated into enclosure 192. In some examples, the mobile phone is separated from other components of system 100 and used independently. When integrated with the other components, system 100, which includes the mobile phone, is configured to measure concentrations of known components in gas samples using an acoustic resonance technique. In specific examples, the speaker of the mobile phone is operable as sound generator 120. The processor of the mobile phone is operable as controller 150. The display of the mobile phone is operable as UI component 170.

Operating Examples

Figure 4:
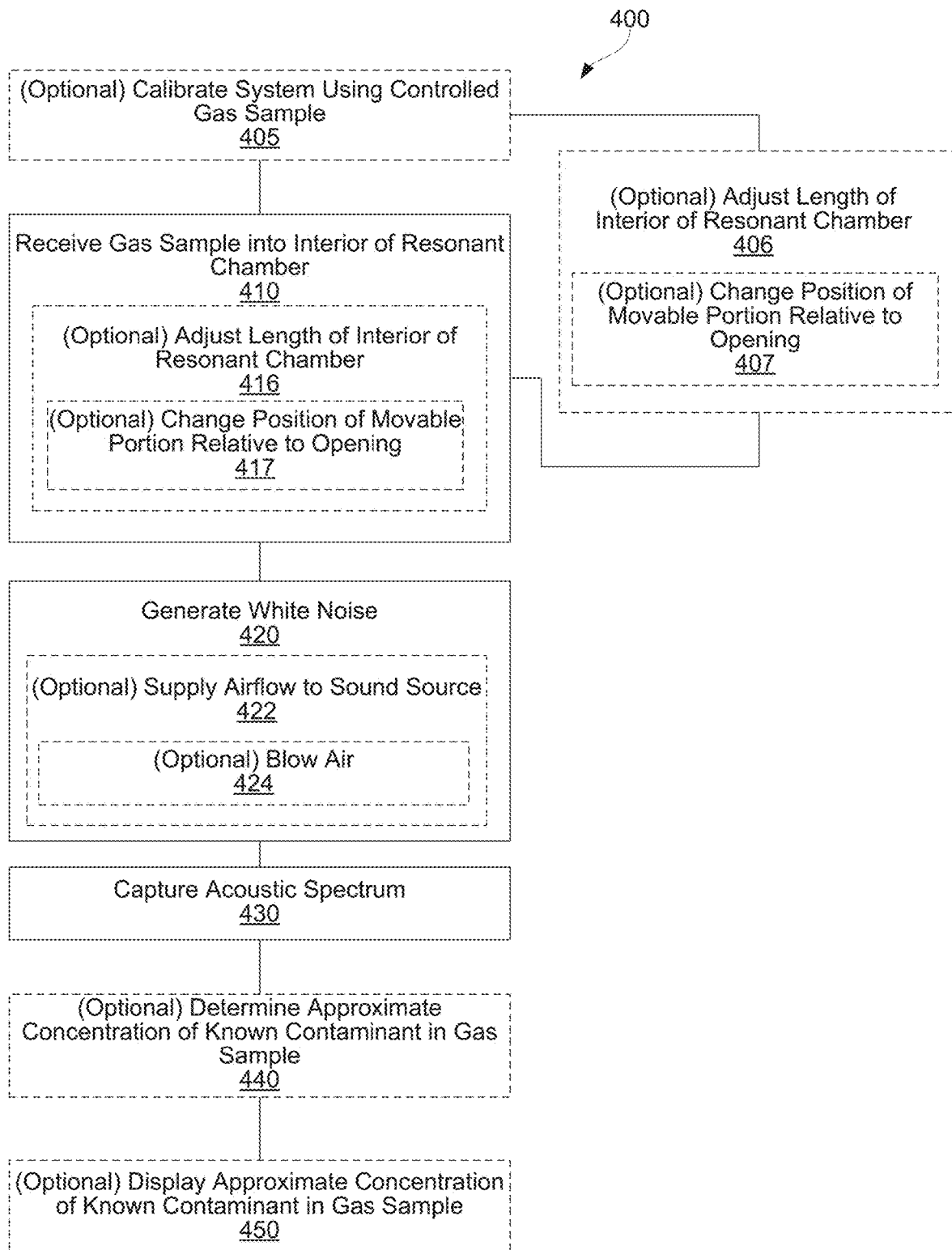
FIG. 4 is a process flowchart corresponding to a method for measuring a concentration of a known component in a gas sample using an acoustic resonance technique, in accordance with some examples.

FIG. 4 is a process flowchart corresponding to method 400 for measuring a concentration of known component in gas sample 200 using system 100, in accordance with some examples. Various examples of system 100, comprising resonant chamber 110, sound generator 120, and an audio sensor 140, are described above.

In some examples, method 400 comprises performing calibration of system 100 using a controlled gas sample (block 405). For example, a referenced gas sample is used in this operation. The referenced gas sample has a known composition and a known molecular weight. Furthermore, in some examples, the referenced gas sample is similar to a tested gas sample. For example, pure air (~78% nitrogen, 21% oxygen, 1% of argon, and negligible amounts of other components) is used as a referenced gas sample when a concentration of a known component in air is later tested for. During calibration, the referenced gas sample is tested in a similar manner as a test gas sample, performing operations represented by block 410, block 420, and block 430 and optionally other operations described below.

In some examples, method 400 comprises receiving the gas sample into interior 114 of resonant chamber 110 (block 410). For example, the gas sample is received through opening 116. In some examples, resonant chamber 110 is placed into an environment, which allows the gas sample to diffuse into interior 114. Alternatively, the gas sample is delivered into interior 114 by creating gas flow. For example, receiving the gas sample into interior 114 of resonant chamber 110 involves adjusting (e.g., increasing) the length of interior 114 of resonant chamber 110 (block 416). Specifically, adjusting the length of interior 114 comprises changing the position of movable portion 113 of wall 112 of resonant chamber 110 relative to opening 116 (block 417). Movable portion 113 is moved away from opening 116, thereby creating a negative pressure inside interior 114 causing the gas sample to flow into interior 114.

Alternatively, adjusting the length of interior 114 of resonant chamber 110 (block 406) and changing the position of movable portion 113 of wall 112 of resonant chamber 110 relative to opening 116 (block 417) are separate operations from receiving the gas sample into interior 114 of resonant chamber 110 (block 410). As described above, the length of interior 114 is adjusted in some examples for a specific target of resonant frequencies.

In some examples, method 400 comprises generating white noise using sound generator 120 (block 420). As described above, sound generator 120 is positioned at and acoustically coupled to opening 116 of resonant chamber 110 such that the white noise propagates to interior 114 of resonant chamber 110. The generated white noise has a continuous spectrum (i.e., a spectrum with no gaps) that has a substantially constant power spectral density over the range of frequencies. However, when the white noise propagates to interior 114 and interacts with the gas sample, the acoustic spectrum changes.

In some examples, generating the white noise comprises supplying airflow to sound source 124 of sound generator 120 (block 422). The airflow is supplied manually (e.g., a user blowing through airflow supply line 125 (block 424)) or using a device (e.g., air compressor, compressed air tank, etc.).

In some examples, method 400 comprises capturing an acoustic spectrum using audio sensor 140 (block 430). As described above, audio sensor 140 is positioned proximate to and in sound communication to opening 116. The captured acoustic spectrum represents interaction of the white noise with the gas sample in interior 114 of resonant chamber 110. More importantly, the captured acoustic spectrum includes a resonant frequency corresponding to the molar mass of the gas sample and, as a result, to the concentration of the known component in the gas sample.

In some examples, the captured acoustic spectrum provides sufficient information and no further analysis is needed. For example, a user observes the resonant frequency in the spectrum and determines (e.g., from a lookup table or experience) the condition of the gas sample. In these examples, the user does not need to know a value of the component concentration.

Alternatively, method 400 comprises optionally determining, from the acoustic spectrum, the concentration of the known component in gas sample 200 (block 440). For example, the concentration is determined using the following formula:

$$Con_{Cont} = \frac{\left(\frac{RF_{Ref}}{RF_{Test}}\right)^2 - 1}{\frac{MM_{Cont}}{MM_{Ref}} - 1},$$

where $Con_{Cont}$ represents the concentration of the known component, $RF_{Ref}$ represents a resonant frequency of a reference sample tested using the system 100, $RF_{Test}$ represents a resonant frequency of the gas sample in the acoustic spectrum, $MM_{Cont}$ represents a molar mass of the known component, and $MM_{Ref}$ represents a molar mass of the reference sample. As described above, this formula is applicable to examples in which a known component is added to a single-component gas sample or a known component evenly dilutes a multi-component gas sample, e.g., relative concentrations of all components are reduced proportionally by the added known component.

In some examples, a known component is added to a multi-component gas sample in such a way that the relative concentrations of all components are reduced differently (e.g., one component of the multi-component gas sample is replaced by the added known component). In these examples, a molar mass of the gas sample is first determined using a formula:

$$MM_{Test} = MM_{Ref} \times \left(\frac{RF_{Ref}}{RF_{Test}}\right)^2,$$

The concentration of the known component is then determined from the molar mass of the gas sample based on a model described below in the experimental results section.

In some examples, method 400 comprises optionally displaying the concentration of the known component in gas sample 220 (block 450). For example, the concentration is displayed on UI component 170 of system 100.

Experimental Results

Figure 5:
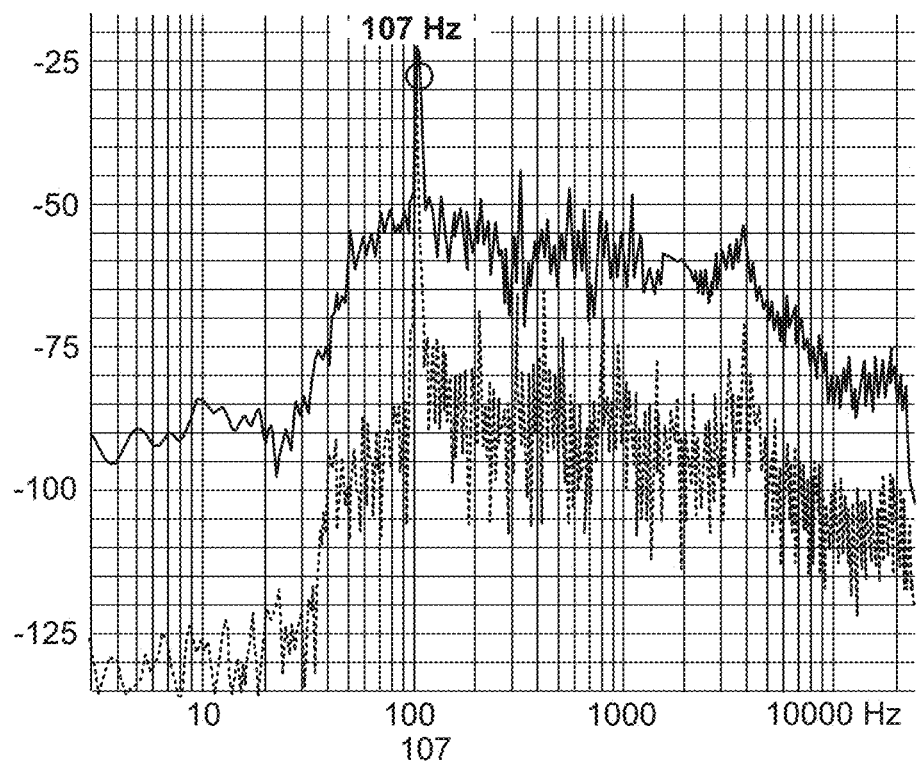
FIGS. 5 and 6 are frequency responses measured by an audio sensor of the system measuring a reference sample and a test sample, respectively.
Figure 6:
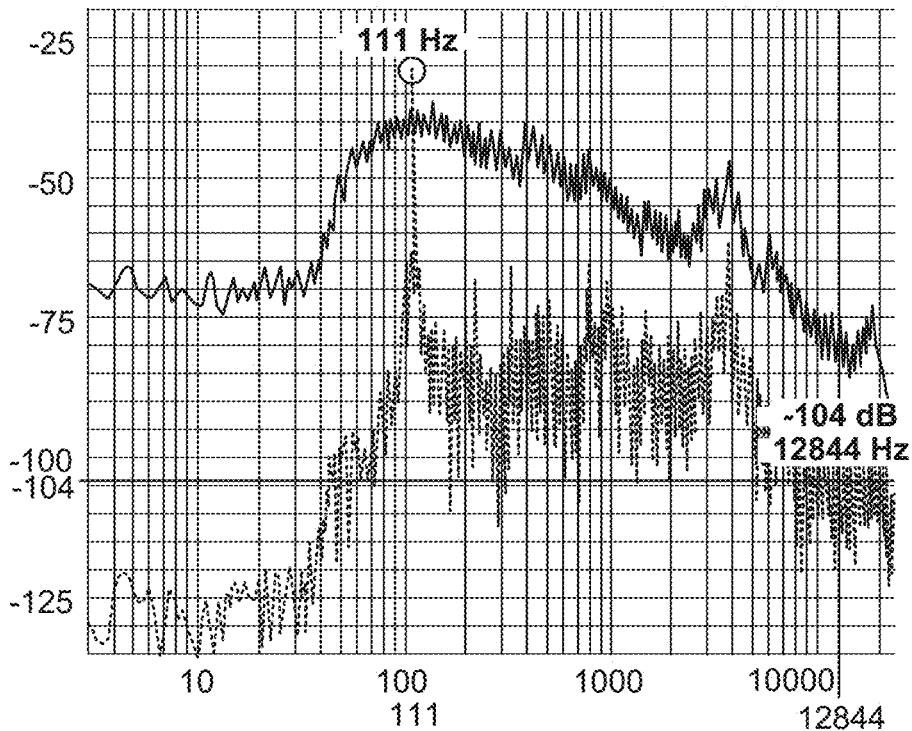

An experiment was conducted using the disclosed method and system to measure concentration of carbon dioxide ($CO_2$) in air. A reference sample was ambient air (~78% nitrogen, 21% oxygen, 1% of argon, and negligible amounts of other components), which has the molar mass ($MM_{ref}$) of 28.97 g/mol. An initial test of the reference sample showed the resonant frequency ($RF_{Ref}$) of 111 Hz, shown in FIG. 5A. A subsequent test of a test sample prepared by replacing most of the oxygen in the reference sample with carbon dioxide showed the resonant frequency (RF $T_{es}$t) of 107 Hz, shown in FIG. 5B. The molar mass ($MM_{Cont}$) of carbon dioxide is 44 g/mol. Calculating the concentration of carbon dioxide in the test sample using Formula 5 presented above yielded the concentration ($Con_{Cont}$) of 14.7%, which is relatively accurate.

However, as stated above, Formula 5 assumes that a uniform part of the reference sample is replaced with a component. In this particular experiment, only oxygen in the reference sample, but not nitrogen, was replaced with carbon dioxide. As such, the molar mass ($MM_{Test}$) of the test sample is first determined using Formula 2 presented above, yielding 31.17 g/mol. The molar mass ($MM_{Test}$) of the test sample, in which only oxygen, but not nitrogen, was replaced with carbon dioxide, would be represented by Formula 6:

$$31.17 \tfrac{g}{mol} = 78\% \times 28 \tfrac{g}{mol} + (21\% - Con_{Cont}) \times 32 \tfrac{g}{mol} + \quad \text{(Formula 6)}$$
$$Con_{Cont} \times 44 \tfrac{g}{mol} + 1\% \times 40 \tfrac{g}{mol}$$

Solving this equation for the concentration ($Con_{Cont}$) of carbon dioxide yields the value of 23.8%, which is also relatively accurate.

Aircraft Examples

In some examples, the apparatus and methods disclosed above are used on aircraft and, more generally, by the aerospace industry. Specifically, the apparatus can be used during fabrication of aircraft as well as during aircraft service and maintenance.

Figure 7:
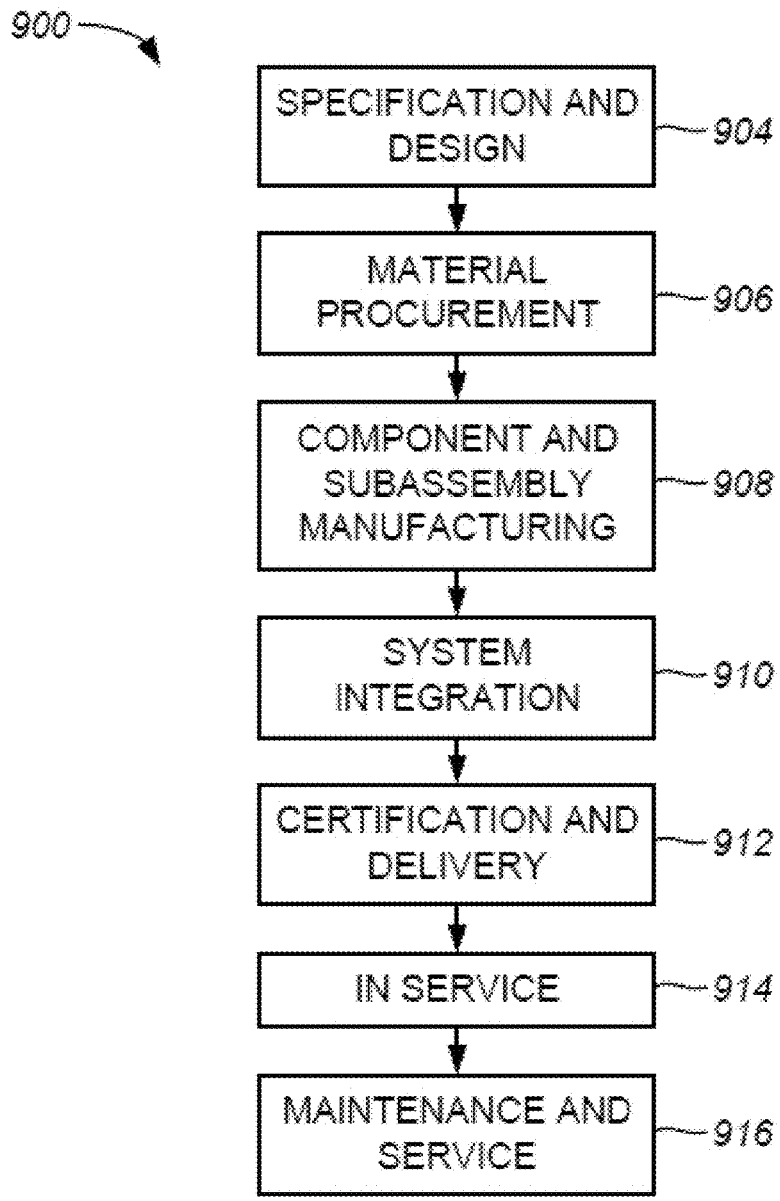
FIG. 7 is a process flowchart corresponding to a method for manufacturing and service the aircraft.
Figure 8:
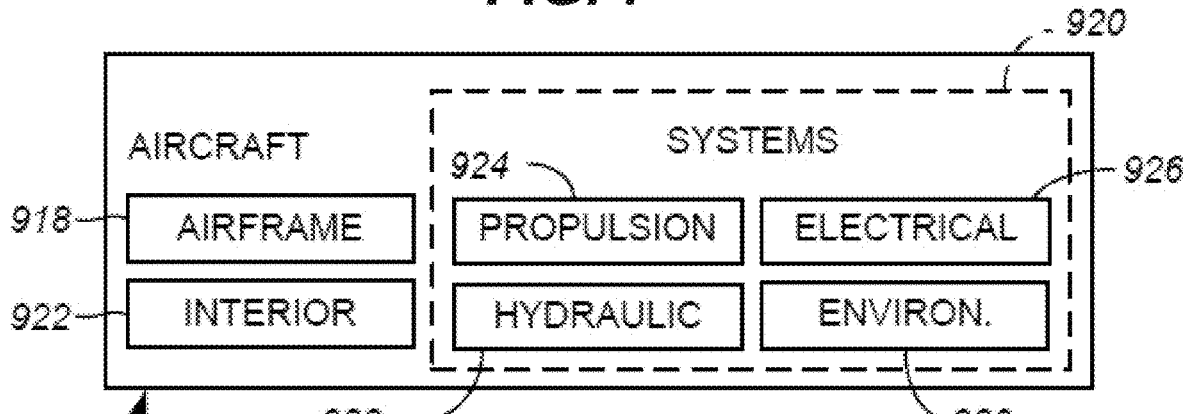
FIG. 8 illustrates a block diagram of an example of an aircraft, in accordance with some examples.

Accordingly, the apparatus and methods disclosed above are applicable for aircraft manufacturing and service method 900 as shown in FIG. 7 and for aircraft 902 as shown in FIG. 8. During pre-production, illustrative method 900 includes specification and design 904 of aircraft 902 and material procurement 906. During production, component and subassembly manufacturing 908 and system integration 910 of aircraft 902 takes place. Thereafter, aircraft 902 goes through certification and delivery 912 in order to be placed in service 914. While in service by a customer, aircraft 902 is scheduled for routine maintenance and service 916 (which also includes modification, reconfiguration, refurbishment, and so on.

In some examples, each of the processes of method 900 is performed or carried out by a system integrator, a third party, and/or an operator (e.g., a customer. For the purposes of this description, a system integrator may include without limitation any number of aircraft manufacturers and major-system subcontractors; a third party may include without limitation any number of venders, subcontractors, and suppliers; and an operator can be an airline, leasing company, military entity, service organization, and so on.

As shown in FIG. 8, aircraft 902 produced by illustrative method 900 includes airframe 918 with plurality of systems 920, and interior 922. Examples of high-level systems 920 include one or more of propulsion system 924, electrical system 926, hydraulic system 928, and environmental system 930. Any number of other systems can be included. Although an aerospace example is shown, the principles of the examples disclosed herein may be applied to other industries, such as the automotive industry.

Apparatus and methods presented herein can be employed during any one or more of the stages of production and service method 900. For example, components or subassemblies corresponding to manufacturing 908 are fabricated or manufactured in a manner similar to components or subassemblies produced while aircraft 902 is in service. Also, one or more apparatus examples, method examples, or a combination thereof may be utilized during manufacturing 908 and system integration 910, for example, by substantially expediting assembly of or reducing the cost of an aircraft 902. Similarly, one or more of apparatus examples, method examples, or a combination thereof may be utilized while aircraft 902 is in service, for example and without limitation, to maintenance and service 916.

CONCLUSION

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatus. Accordingly, the present examples are to be considered as illustrative and not restrictive.

What is claimed is:

1. A system for measuring a concentration of a known component in a gas sample using an acoustic resonance technique, the system comprising:
   a resonant chamber, comprising a wall, forming an interior, and an opening extending through the wall to the interior;
   a sound generator, positioned at and acoustically coupled to the opening of the resonant chamber and configured to generate white noise and supply the white noise into the interior of the resonant chamber; and
   an audio sensor, positioned proximate to and in sound communication to the opening and configured to measure an acoustic spectrum emitted from the interior of the resonant chamber through the opening.

2. The system of claim 1,
   wherein the wall of the resonant chamber comprises a movable portion, opposite of the opening and slidably coupled to a fixed portion of the wall,
   wherein the opening and the movable portion define a length of the interior of the resonant chamber; and
   wherein the length of the interior is controllably adjustable.

3. The system of claim 2,
   wherein the resonant chamber comprises two or more markings; and
   wherein each of the two or more markings represents a resonant wavelength, corresponding to the length of the interior.

4. The system of claim 3,
   wherein the wall is formed by a transparent syringe; and
   wherein the movable portion is formed by a piston.

5. The system of claim 1, wherein the sound generator is selected from a group consisting of:
   an electronic sound generator,
   a combination of a sound source and an airflow generator; and
   a combination of a sound source and an airflow supply line.

6. The system of claim 5, wherein the sound source is a reed.

7. The system of claim 5, wherein the airflow generator is selected from the group consisting of a syringe, a compressed air tank, and a compressor.

8. The system of claim 1, further comprising a computer system such that the audio sensor is a part of the computer system and such that the resonant chamber and the sound generator are connected to and supported by the computer system.

9. The system of claim 8, wherein the computer system comprises a controller for analyzing the acoustic spectrum and determining the concentration of the known component in the gas sample.

10. The system of claim 8, wherein the computer system is a mobile phone further comprising an enclosure; and
    wherein the resonant chamber and the sound generator are integrated into the enclosure.

11. A method for measuring a concentration of a known component in a gas sample using a system, comprising a resonant chamber, a sound generator, and an audio sensor, the method comprising:
    receiving the gas sample into an interior of the resonant chamber;
    generating white noise using the sound generator, positioned at and acoustically coupled to an opening of the resonant chamber such that the white noise propagates to the interior of the resonant chamber; and
    capturing an acoustic spectrum using the audio sensor, positioned proximate to and in sound communication to the opening, wherein the acoustic spectrum represents interaction of the white noise with the gas sample received in the interior of the resonant chamber and corresponds to the concentration of the known component in the gas sample.

12. The method of claim 11, further comprising determining, from the acoustic spectrum, the concentration of the known component in the gas sample.

13. The method of claim 12,
    wherein determining the concentration of the known component in the gas sample is performed using a formula $$Con_{Cont} = \frac{\left(\frac{RF_{Ref}}{RF_{Test}}\right)^2 - 1}{\frac{MM_{Cont}}{MM_{Ref}} - 1},$$

wherein $Con_{Cont}$ represents the concentration of the known component,
wherein $RF_{Ref}$ represents a resonant frequency of a reference sample tested using the system 100,
wherein $RF_{Test}$ represents a resonant frequency of the gas sample in the acoustic spectrum,
wherein $MM_{Cont}$ represents a molar mass of the known component; and
wherein $M_{Ref}$ represents a molar mass of the reference sample.

14. The method of claim 11, further comprising:
    determining a molar mass of the gas sample using a formula $$MM_{Test} = MM_{Ref} \times \left(\frac{RF_{Ref}}{RF_{Test}}\right)^2,$$

wherein $RF_{Ref}$ represents a resonant frequency of a reference sample tested using the system 100,
wherein $RF_{Test}$ represents a resonant frequency of the gas sample in the acoustic spectrum, and
wherein $MM_{Ref}$ represents a molar mass of the reference sample; and
determining the concentration of the known component in the gas sample from the molar mass of the gas sample.

15. The method of claim 11, further comprising performing a calibration of the system using a reference sample, thereby determining a resonant frequency of the reference sample.

16. The method of claim 15, wherein the known component replaces one or more components in the reference sample, thereby forming the gas sample.

17. The method of claim 15, wherein the known component proportionally replaces all components in the reference sample, thereby forming the gas sample.

18. The method of claim 11, further comprising displaying the concentration of the known component in the gas sample on a user interface (UI) component of the system.

19. The method of claim 11, further comprising adjusting a length of the interior of the resonant chamber.

20. The method of claim 19, wherein adjusting the length of the interior comprises changing a position of a movable portion of a wall of the resonant chamber relative to the opening.

21. The method of claim 20, wherein receiving the gas sample into the interior of the resonant chamber comprises changing the position of the movable portion of the wall relative to the opening.

22. The method of claim 11, wherein generating the white noise comprises supplying an airflow to a sound source of the sound generator.

\* \* \* \* \*